United States Patent [19]

Schwabe

[11] Patent Number: 5,512,286
[45] Date of Patent: Apr. 30, 1996

[54] EXTRACT FROM LEAVES OF GINKGO BILOBA FOR INTRAVENOUS INJECTION OR INFUSION

[75] Inventor: Klaus-Peter Schwabe, Karlsruhe, Germany

[73] Assignee: Dr. Willmar Schwabe GmbH & Co., Karlsruhe, Germany

[21] Appl. No.: 200,378

[22] Filed: Feb. 23, 1994

Related U.S. Application Data

[63] Continuation of Ser. No. 766,929, Sep. 27, 1991, abandoned.

[30] Foreign Application Priority Data

Sep. 28, 1990 [DE] Germany .......................... 40 30 758.1

[51] Int. Cl.⁶ .................................................. A61K 35/78
[52] U.S. Cl. .................................................. 424/195.1
[58] Field of Search ........................................... 424/195.1

[56] References Cited

U.S. PATENT DOCUMENTS 4,753,929  6/1988  Matsumoto ................................ 514/27

FOREIGN PATENT DOCUMENTS

| 0086315 | 8/1983 | France . |
| 2117429 | 5/1981 | Germany .......................... 424/195.1 |
| 3802895 | 8/1989 | Germany . |
| 62-076348 | 2/1987 | Japan . |
| 63-033029 | 5/1988 | Japan . |
| 2-161327 | 4/1990 | Japan . |
| 02104530 | 4/1990 | Japan ................................ 424/195.1 |

OTHER PUBLICATIONS

The Merck Index 10th ed Merck & Co, Rattway N.J. 1983 #5569.
Attella, M. J., Ginrgo Biloba Extract Facilitates . . . Experimental Neurology 105, 62–71 (1989).

*Primary Examiner*—Ralph J. Gitomer
*Attorney, Agent, or Firm*—Kenyon & Kenyon

[57] ABSTRACT

The present application relates to an extract from the leaves of Ginkgo biloba containing most of the flavone glycosides, ginkgolides and bilobalide originally present in the leaves, characterized in that it is essentially free of components of the leaves with serum-precipitating and/or haemagglutinating properties, method of its preparation and pharmaceutical compositions containing the extract.

20 Claims, No Drawings

EXTRACT FROM LEAVES OF GINKGO BILOBA FOR INTRAVENOUS INJECTION OR INFUSION

This application is a continuation, of application Ser. No. 07/766,929, filed Sep. 27, 1991, now abandoned.

The invention relates to an extract from the leaves of Ginkgo biloba which is free of components with serum-precipitating and/or haemagglutinating properties and a method for its preparation.

The extract of the invention is especially suitable for the preparation of pharmaceuticals for intravenous administration, such as intravenous injection or infusion, since it does not contain components with serum-precipitating and/or haemagglutinating properties which disturb such an application. The invention therefore also relates to ampoule preparations containing the extract of the invention which are directed to intravenous administration.

DE-B-21 17 429 describes a method of preparation of an active component mixture from the leaves of Ginkgo biloba as well as an injection or infusion preparation from this mixture with an active component concentration of 3.5 mg/ml for example.

Further embodiments of this method, the aim of which is to separate components with allergenic potential from the extracts, are described in the patent applications P 39 40 092.1 and P 39 40 091.3 which are not prepublished.

In the case of injection solutions with a higher content of the active component mixture prepared according to the method of DE-B-21 17 429, according to the above-cited patent applications P 39 40 092.1 and P 39 40 091.3 or according to another known method, lines of precipitation are observed on testing for serum-precipitating properties above a concentration of 25 mg/ml in the test medium.

Furthermore, the above-mentioned extracts of Ginkgo biloba already have haemagglutinating properties at concentrations below 10 mg/ml which prevent their use as pharmaceuticals for intravenous administration.

Consequently, it is an object of the present invention to prepare an extract from the leaves of Ginkgo biloba which contains most of the flavone glycosides, ginkgolides and bilobalide originally present in the leaves and essentially show no serum-precipitating and/or haemagglutinating properties. Extracts for therapeutic use according to the practice of the invention may comprise between 22 and 26 weight percent of flavone glycosides. Additionally, extracts according to the practice of the invention may comprise less than 1 ppm of alkylphenol compounds.

A further object of the invention is to provide a method of preparation of the above extracts from the leaves of Ginkgo biloba which allows the provision of extracts containing the active components with the pharmaceutically and clinically desired effect but not the components with serum-precipitating and/or haemagglutinating properties.

Finally, it is an object of the present invention to prepare pharmaceutical preparations, in particular ampoule preparations, for intravenous injection or infusion which contain the above Ginkgo biloba extracts and the application of which poses no danger of side effects caused by components with serum-precipitating and/or haemagglutinating properties.

Consequently, the invention relates to an extract from the leaves of Ginkgo biloba according to claims 1 to 5 which is practically free of components with serum-precipitating and haemagglutinating properties.

In addition, the invention relates to a method of preparation of the above Ginkgo biloba extracts according to any of claims 6 to 12 in which the leaves of Ginkgo biloba are extracted in a manner known per se in order to obtain an extract containing the components of the leaves, whereby in the course of the extraction process or after this process a chromatographic treatment is carried out on a cross-linked polyvinyl pyrrolidone or a polyamide.

Methods of obtaining the components from the leaves of Ginkgo biloba are described inter alia in DE-B-21 17 429 and the German patent applications nos. P 39 40 091.3 and P 39 40 092.1. The treatment with polyamide (Nylon-6®)-powder according to Example 3 of DE-B-21 17 429 by batch process serves to remove the undesired polymeric polyphenol compounds and does not allow the preparation according to the invention of extracts from the leaves of Gingko Biloba which are essentially free of components with serum-precipitating and/or haemagglutinating properties.

EP-A-86 315 describes a method of reducing the content of polymeric polyphenol compounds by means of polyvinyl pyrrolidone in ethanolic-aqueous solution by batch process. The removal of the extract components having the serum-precipitating and haemagglutinating effect as described in the present invention is not achieved by this method either.

According to an embodiment of the invention, an extract from the leaves of Ginkgo biloba containing most of the flavone glycosides, ginkgolides and bilobalide originally present in the leaves is provided. This extract comprises 20 to 30 weight percent, preferably 22 to 26 weight percent, flavone glycosides, 2.5 to 4.5 weight percent ginkoglides selected from ginkgolide A, B, C and J and mixtures thereof, 2.0 to 4.0 weight percent bilobalide and less than 10 ppm alkylphenol compounds. The extract is also essentially free of components of the leaves with serum-precipitating or hemagglutinating properties.

According to an embodiment of the invention, an extract from the leaves of Ginkgo biloba containing most of the flavone glycosides, ginkgolides and bilobalide originally present in the leaves is provided. This extract comprises 20 to 30 weight percent, preferably 22 to 26 weight percent, flavone glycosides, 2.5 to 4.5 weight percent ginkgolides selected from ginkgolide A, B, C and J and mixtures thereof, 2.0 to 4.0 weight percent bilobalide and less than 10 ppm alkylphenol compounds. The extract is also essentially free of components of the leaves with serum-precipitating or hemagglutinating properties.

According to another embodiment of the invention, a method is provided for preparing the extract of the prior paragraph. This method comprises the following steps:

(a) fresh or dried green leaves from Ginkgo biloba are extracted at a temperature of approximately 40° to 100° C. with an organic solvent selected from the group consisting of aqueous acetone, an aqueous alkanol with 1 to 3 C-atoms and anhydrous methanol, (b) most of the organic solvent is separated by a distillation step from the extract to a maximum organic solvent content of 10 weight percent, preferably a maximum of 5 weight percent, whereby water is added, optionally, near the end of the distillation step, to form a concentrated solution, (c) the concentrated solution of step (b) is diluted with water to a solids content of 5–25 weight percent, preferably 15 to 20 weight percent, allowed to cool, while being stirred, to a temperature below 25° C., preferably of approximately 10° to 12° C., until a precipitate forms and this precipitate, consisting of lipophilic components which do not dissolve well in water, is removed to form a filtered solution, (d) ammonium sulfate is added to the filtered solution to achieve an ammonium sulfate content of 30 weight percent and the solution formed is extracted with methylethylketone or a mixture containing methylethylketone and acetone in a ratio of 9:1 to 4:6, preferably 6:4, to form a methylethylketone containing extract, (e) the methylethylketone containing extract is concentrated to a solids content of 50–70% and is diluted with water to a solids content of 5–20%, forming a diluted solution, (f) the diluted solution is subjected to a multistep extraction with water-immiscible butanol or pentanol to form a butanol or pentanol phase, (g) the butanol or pentanol phase is concentrated to a solids content of 50–70% to form a concentrate, (h) the concentrate is diluted with sufficient water and ethanol to obtain an aqueous alcohol solution of 5 to 20 weight percent dry extract in 20 to 60 weight percent aqueous ethanol, (i) the aqueous alcohol solution is extracted with an aliphatic or cycloaliphatic solvent with a boiling point of approximately 60° to 100° C. to further remove the alkylphenol compounds, forming a water phase, (j) the water phase is concentrated under reduced pressure to form a concentrate, (k) the concentrate is taken up in a mixture of water and acetone in a ratio of 10:90 to 60:40 weight percent, fed onto a column filled with a cross-linked polyvinyl pyrrolidone substrate and eluted with the mixture of water and acetone in a ratio of 10:90 to 60:40 weight percent to produce an eluate, and (1) the eluate is dried at a maximum temperature of 60 to 80° C. to a dry extract with a water content of less than 5%.

The chromatographic treatment according to the present invention can be carried out on a cross-linked polyvinyl pyrrolidone or a polyamide; cross-linked polyvinyl pyrrolidone is preferred. Of the eluants used according to the present invention a mixture of water and a $D_{1-4}$-alcohol, or a mixture of water and a $C_{3-4}$-ketone are preferred. Eluant used according to the present invention may include a moisture of water and a $C_{1-14}$-alcohol. Examples of chromatographic treatment according to the present invention are found in Example 5 through Example 8.

Especially preferred is a mixture of water and acetone in a ratio of 10:90 to 60:40, in particular in a ratio of 20:80 to 50:50.

Finally, the present invention relates to pharmaceutical compositions according to any of claims 13 to 15, in particular in the form of ampoule preparations. In a preferred embodiment the pharmaceutical preparations are characterized by a content of Ginkgo biloba extract prepared according to a method of the invention in lyophilised form.

For the experiments described below for serum-precipitating and/or haemagglutinating properties, extracts were used which had been prepared according to the method of the German patent application P 39 40 091.3 or modified according to the teaching of the present invention.

A method representative of known extraction methods useful to prepare starting material for the processes of the invention is provided below as Example 4.

For the testing of serum-precipitating properties, a modified, double gel diffusion test was carried out according to Ouchterlony (Progress in Allergy, Vol. V (1958) 1).

The experiment is carried out in a 1% agar gel in phosphate buffered sodium chloride solution (PBS; NaCl 120 mM, KCl 2.7 mM, sodium phosphate 10 mM, pH 7.4) with 0.02% $NaN_3$ on an electrophoresis film. In a circular arrangement a central hole is filled with 10 μl of undiluted human serum and six peripheral cavities at a distance of 8 mm are each filled with 10 μl of an extract solution (PBS) in a concentration of 25 or 50 mg/ml.

The test preparations are incubated for 24 hours at room temperature in a damp chamber and subsequently evaluated in their native state and after being stained with Coomassie blue R 250. For the purpose of comparison both negative and positive controls are examined in parallel preparations. The lack of any line of precipitation in the case of the highest extract concentration used proves the absence of serum-precipitating accompanying substances.

TABLE 1

Testing for serum precipitating properties

| Extract No. | Concentration (mg/ml) | |
| --- | --- | --- |
| | before | after |
| | chromatographical treatment | |
| 1 | 50 ++ | – |
| | 25 + | – |
| 2 | 50 ++ | – |
| | 25 + | – |
| 3 | 50 ++ | – |
| | 25 + | – |
| 4 | 50 ++ | – |
| | 25 + | – |

++ two lines of precipitation; + one line of precipitation;
– no line of precipitation In addition to the examination of serum-precipitating properties, the extracts according to the invention were examined for haemagglutinating properties. Solutions of active component mixtures from the prior art when testing for haemagglutinating properties according to the test method described in the following already show an agglutination of the human erythrocytes used at a concentration below 10 mg/ml in the test medium.

The object of the examination for haemagglutinating properties is to check the presence of accompanying substances which cause clumping of blood cells. The test is carried out in V-shape micro titre plates. Each cavity is filled with 50 μl of a suspension of 2% human erythrocytes (ABO-type A) in phosphate buffered sodium chloride solution (PBS; CaCl 120 mM, KCl 2.7 mM, sodium phosphate 10 mM, pH 7.4). Subsequently, 50 μl of solutions containing Ginkgo biloba extract are added in concentrations decreasing by factor 2 in the range of 50 mg/ml to 0.78 mg/ml in PBS and the preparation is mixed for approximately 30 seconds on a shaker.

After an incubation time of 60 minutes at room temperature, the reaction is evaluated by means of a magnifying glass and compared with the results of simultaneously examined positive and negative controls. A lack of clumping of the erythrocytes in the case of concentrations of up to 25 mg/ml is considered to be sufficient removal of substances with haemagglutinating properties. According to the present invention, however, extracts can be prepared which show no clumping of erythrocytes up to a concentration of 50 mg/ml.

TABLE 2

Testing for haemagglutinating effect

| Extract No. | Concentration (mg/ml)* | |
| --- | --- | --- |
| | before | after |
| | chromatographical treatment | |
| 1 | 6.25 | 25.0 |
| 2 | 6.25 | 50.0 |
| 3 | 6.25 | 50.0 |
| 4 | 3.13 | 25.0 |

TABLE 2-continued

Testing for haemagglutinating effect
Concentration (mg/ml)*

| Extract No. | before chromatographical treatment | after |
|---|---|---|

*The lowest concentration in each case is stated in which a positive reaction can still be established.

The above-mentioned interactions with soluble and corpuscular components of the blood can lead to side effects or complications when using injection solutions with comparable concentrations of active component mixtures from the leaves of Ginkgo biloba if the components with serum-precipitating and/or haemagglutinating properties are not removed according to the method of the present invention.

The examples illustrate the invention. Parts and percentage data refer to weight unless otherwise stated.

EXAMPLE 1

10 kg of cross-linked polyvinyl pyrrolidone is stirred with 90 kg of 75% aqueous acetone for one hour and then allowed to stand at room temperature for approx. 16 hours. The suspension is poured into a 100 l glass cylinder with a sieve plate and at least 70 kg of solvent is collected as a forerun. 30 kg of Ginkgo extract with approx. 24% flavone glycosides is dissolved in 90 kg of 75% aqueous acetone and fed onto the column. Elution is carried out with 75% aqueous acetone until the extract concentration in the eluate is less than 0.5%.

The combined eluate fractions are filtered and concentrated in vacuum to a solids content of 40–60%. This concentrate is dried in a vacuum drying oven to a dry extract.

EXAMPLE 2

1 Vial contains in lyophilised form:

| Ginkgo biloba extract | 50.0 mg |
|---|---|
| Mannitol | 94.7 mg |

The pH value is adjusted with 6N NaOH to pH 4.0–4.4.
The corresponding solvent ampoule contains:

| $Na_2HPO_4 \times 12\ H_2O$ | 26.0 mg |
|---|---|
| water for injection purposes | 2974.0 mg |

EXAMPLE 3

1 Vial contains in lyophilised form:

| Ginkgo biloba extract | 200.0 mg |
|---|---|
| Mannitol | 378.8 mg |

The pH value is adjusted with 6N NaOH to pH 4.0–4.4.
The corresponding solvent ampoule contains:

| $Na_2HPO_4 \times 12\ H_2O$ | 86.40 mg |
|---|---|
| water for injection purposes | 9913.60 mg |

EXAMPLE 4

100 kg of dry Ginkgo biloba leaves are crushed in a mill to a particle size of less than 4 mm. After adding 750 kg of 60 weight percent aqueous acetone the mixture is stirred intensively for 30 minutes at a temperature of 57° to 59° C. The solid residue is separated by filtration or centrifugation and subjected to a second extraction under the same conditions. The extracts from the first and second extraction steps are combined. The ginkgolic acid content (based on the dry extract) equals approximately 13,000 ppm. The extract is concentrated under reduced pressure to a solids content of 30 to 40% and a maximum of approximately 5 weight percent acetone. By adding water, the concentration is diluted to double volume and, while being stirred, left to cool to approximately 12° C. A precipitate forms which contains most of the ginkgolic acids, that is, the alkylphenol compounds, present in the leaves. After one hour at this temperature, the resultant precipitate is separated by centrifugation and discarded.

The ginkgolic acid content in the resultant aqueous supernatant (based on the dry extract) equals approximately 320 ppm.

30 parts of ammonium sulfate are added to 100 parts of the aqueous solution. The mixture is stirred. After the ammonium sulfate has dissolved, a liquid-liquid-extraction is carried out twice with a mixture of methylethylketone and acetone in a ratio of 6:4 to 1:1, whereby the organic solvent added is the equivalent of half the volume of the aqueous solution and, after intensive stirring and pumping, the organic upper phase formed on completion of the mixing process is removed.

The methylethylketone acetone solution is then concentrated under reduced pressure to a solids content of 50 to 70%. This concentrate is diluted with water and 95 weight percent ethanol so that a solution with 10 weight percent dry extract in 50 weight percent aqueous ethanol is obtained. While stirring intensively, an aqueous solution of lead hydroxide acetate is added in small quantities to this solution until there is a change in colour from brown to umber (brown with a green cast). The lead-tannin precipitate which forms is separated by centrifugation.

The supernatant from the lead-tannin precipitation is subjected to a liquid-liquid-extraction with n-hexane in order to further remove the alkylphenol compounds. In this step, the alcohol-aqueous filtrate is stirred at least three times at room temperature, each time with ⅓ of its volume of n-hexane.

The aqueous-alcohol extract solution is then concentrated under reduced pressure to an ethanol content of less than approximately 5%. 20 parts of ammonium sulfate are dissolved in 100 parts of this solution and then a liquid-liquid-extraction is carried out with a mixture of methylethylketone and ethanol in a volumetric ratio of 6:4, whereby extraction with the organic solvent mixture is carried out twice, each time with the equivalent of half the volume of the aqueous solution. The organic phase is separated and stirred with 20% of its weight of ammonium sulfate. A possible phase of water and the undissolved ammonium sulfate are removed.

The clear extract solution is concentrated to a solids content of 50 to 70 weight percent. This concentrate is dried under reduced pressure at a maximum product temperature of approximately 60° to 80° C. to a dry extract with a water content of less than 5%.

From 100 kg of Ginkgo leaves, 2.5 kg of Ginkgo biloba extract with a content of approximately 24 weight percent flavone glycosides, approximately 3.6 weight percent ginkgolides, approximately 2.9 weight percent bilobalide, approximately 6.5 weight percent proanthocyanidins and less than 1 ppm alkylphenol compounds are obtained.

EXAMPLE 5

This Example provides a method for preparing an extract from Ginkgo biloba leaves, comprising 20 to 30 weight percent, in particular 22 to 26 weight percent, flavone glycosides, 2.5 to 4.5 weight percent of ginkgolides A, B, C and J in total, 2.0 to 4.0 weight percent bilobalide and less than 10 ppm, in particular less than 1 ppm, alkylphenol compounds, said extract being essentially free of components of the leaves with serum-precipitating and/or hemagglutinating properties. The method is as follows:

(a) fresh or dried green leaves from Ginkgo biloba are extracted at a temperature of approximately 40° to 100° C. with either aqueous acetone, an aqueous alkanol with 1 to 3 C-atoms or anhydrous methanol, (b) most of the organic solvent is separated from the extract to a maximum content of 10 weight percent, preferably a maximum of 5 weight percent, whereby water can be added in the last distillation steps, (c) the remaining concentrated aqueous solution is diluted with water to a solids content of 5–25 weight percent, preferably 15 to 20 weight percent, allowed to cool, while being stirred, to a temperature below 25° C., preferably of approximately 10° to 12° C., until a precipitate forms and this precipitate, consisting of lipophilic components which do not dissolve well in water, is removed, (d) ammonium sulfate is added to the remaining aqueous solution to give a content of 30 weight percent and the solution formed is extracted with methylethylketone or a mixture containing methylethylketone and acetone in a ratio of 9:1 to 4:6, preferably 6:4, (e) the extract obtained is concentrated to a solids content of 50–70% and the resultant concentrate is diluted with water to a solids contents of 5–20%, (f) the resultant solution is subjected to a multistep extraction with a water-immiscible butanol or pentanol, (g) the butanol or pentanol layers are concentrated to a solids content of 50–70%, (h) the concentrate is diluted with sufficient water and ethanol to obtain a solution of 5 to 20 weight percent dry extract in 20 to 60 weight percent aqueous ethanol, (i) the aqueous alcohol solution is extracted with an aliphatic or cycloaliphatic solvent with a boiling point of approximately 60° to 100° C. in order to further remove the alkylphenol compounds, (j) the water phase is concentrated under reduced pressure, (k) the resultant concentrate is taken up in a mixture of water and acetone in a ratio of 10:90 to 60:40 weight percent, fed onto a column (see Example 1 for representative preparation thereof) filled with a cross-linked polyvinyl pyrrolidone and eluted with the above mixture of water and acetone, and (l) the eluate is dried at a maximum temperature of 60 to 80° C. to a dry extract with a water content of less than 5%.

EXAMPLE 6

Additional variations on the method of Example 5 are possible, for example, the method steps (d) and (e) thereof are left out and the aqueous solution obtained in (c) thereof is processed further according to steps (f) to (l) thereof, whereby in step (f) thereof 10 to 30 weight percent of sodium chloride or ammonium sulfate, preferably 20% ammonium sulfate, can be added to the aqueous solution.

EXAMPLE 7

The method according to Example 5 or 6, wherein n-butanol is used in step (f) thereof.

EXAMPLE 8

The method according to Example 5, wherein instead of method steps (e) to (l) thereof the following new method steps (e) to (l) are carried out:

(e) the extract obtained is concentrated to a solids content of 50–70% and the concentrate obtained is diluted with water and ethanol so that a solution is obtained which contains 50 weight percent of water and 50 weight percent of ethanol with a solids content of 10 weight percent, (f) an aqueous solution of a lead salt such as lead acetate, lead hydroxide acetate or lead nitrate, or an aqueous suspension of lead hydroxide, preferably a solution of lead hydroxide acetate, is added to the thus obtained solution until a change in color from brown to umber takes place, and the precipitate formed is removed, (g) the remaining aqueous-alcohol solution is extracted with an aliphatic or cycloaliphatic solvent with a boiling point of approximately 60° to 100° C. in order to further remove the alkylphenol compounds, (h) the remaining aqueous-alcohol solution is concentrated under reduced pressure to a maximum ethanol content of approximately 5% and ammonium sulfate is added up to a content of 20 weight percent, (i) the solution obtained is extracted with a mixture of methylethylketone and ethanol in a ratio of 8:2 to 5:5, preferably 6:4, and (j) the resultant organic phase is concentrated to a solids content of 50 to 70 weight percent, (k) the resultant concentrate is taken up in a mixture of water and acetone in a ratio of 10:90 to 60:40 weight percent, fed onto a column filled with a cross-linked polyvinyl pyrrolidone and eluted with the above mixture of water and acetone, and (l) the eluate is dried at a maximum temperature of 60° to 80° C. to a dry extract with a water content of less than 5%.

I claim:

1. An extract from the leaves of Ginkgo biloba containing most of the flavone glycosides, ginkgolides and bilobalide originally present in the leaves, comprising 20 to 30 weight percent flavone glycosides, 2.5 to 4.5 weight percent ginkgolides selected from the group consisting of ginkgolide A, B, C and J and mixtures thereof, 2.0 to 4.0 weight percent bilobalide and less than 10 ppm alkylphenol compounds, said extract being essentially free of components of the leaves with serum-precipitating or hemagglutinating properties.

2. An extract according to claim 1 that does not cause agglutination of human erythrocytes when tested in a hemagglutinating procedure at a concentration of 10 mg/ml in test medium.

3. An extract according to claim 1 obtained by an extraction process from the leaves of Ginkgo biloba, said extraction process including a chromatographic treatment carried out on a cross-linked polyvinyl pyrrolidone or a polyamide substrate.

4. An extract according to claim 3, wherein said chromatographic treatment is carried out with a mixture of water and a $C_{1-4}$-alcohol, or a mixture of water and a $C_{3-4}$-ketone, as an eluant.

5. An extract according to claim 4, wherein said chromatographic treatment is carried out with a mixture of water and acetone in a ratio of 10:90 to 60:40.

6. An extract according to claim 1 comprising 22 to 26 weight percent flavone glycosides.

7. An extract according to claim 1 comprising less than 1 ppm alkylphenol compounds.

8. A pharmaceutical composition comprising an extract of the leaves of Ginkgo biloba according to claim 1 and a pharmaceutically acceptable carrier, wherein said pharmaceutical composition is essentially free of components of said leaves causing serum-precipitation or hemagglutination, as measured in a serum-precipitation or hemagglutination test at a concentration of said extract therein, of up to 50 mg/ml.

9. A pharmaceutical composition comprising an extract of the leaves of Ginkgo biloba according to claim 1 and a pharmaceutically acceptable carrier, wherein said pharmaceutical composition is essentially free of components of said leaves causing serum-precipitation or hemagglutination, as measured in a serum-precipitation or hemagglutination test at a concentration of said extract therein, of 10 mg/ml or more.

10. An extract according to claim 1 obtained by a process of extraction from the leaves of Ginkgo biloba wherein said extraction includes also a chromatographic treatment carried out with a crosslinked polyvinyl pyrrolidone or a polyamide substrate wherein a mixture of water and a $C_{1-4}$-alcohol is used as eluant therefor.

11. An extract according to claim 1 obtained by a process of extraction from the leaves of Ginkgo biloba wherein said extraction includes also a chromatographic treatment carried out with a crosslinked polyvinyl pyrrolidone or a polyamide substrate wherein a mixture of water and a $C_{3-4}$-ketone is used as eluant therefor.

12. A pharmaceutical composition for intravenous injection or infusion comprising a Ginkgo biloba extract according to claim 1 and a pharmaceutically acceptable carrier.

13. The pharmaceutical composition according to claim 12, wherein the Ginkgo biloba extract and the pharmaceutically acceptable carrier are provided in an ampoule.

14. The pharmaceutical composition according to claim 13 wherein the ampoule contains 10 to 50 weight percent of the Ginkgo biloba extract and 50 to 90 weight percent of mannitol as the pharmaceutically acceptable carrier.

15. A method for preparing an extract from Ginkgo biloba leaves, comprising 20 to 30 weight percent flavone glycosides, 2.5 to 4.5 weight percent of ginkgolides selected from the group consisting of ginkgolide A, B, C and J and mixtures thereof, 2.0 to 4.0 weight percent bilobalide and less than 10 ppm of alkylphenol compounds, which is essentially free of components of the leaves with serum-precipitating or hemagglutinating properties, wherein (a) fresh or dried green leaves from Ginkgo biloba are extracted at a temperature of approximately 40 to 100° C. with an organic solvent selected from the group consisting of aqueous acetone, an aqueous alkanol with 1 to 3 C-atoms and anhydrous methanol to form an extract, (b) most of the organic solvent in said extract of step (a) is separated by a distillation step to a maximum organic solvent content of 10 weight percent, whereby water is optionally added near the end of the distillation step, to form a concentrated solution, (c) the concentrated solution of step (b) is diluted with water to a solids content of 5–25 weight percent, allowed to cool while being stirred to a temperature below 25° C. until a precipitate forms, and this precipitate, consisting of lipophilic components which do not dissolve well in water, is removed to form a filtered solution, (d) ammonium sulfate is added to the filtered solution to achieve an ammonium sulfate content of 30 weight percent to form an ammonium sulfate solution which is extracted with methylethylketone or a mixture containing methylethylketone and acetone in a ratio of 9:1 to 4:6 to form a methylethylketone containing extract, (e) the methylethylketone containing extract is concentrated to a solids content of 50–70% and is diluted with water to a solids content of 5–20%, forming a diluted solution, (f) the diluted solution is subjected to an extraction with butanol or pentanol to form a butanol or pentanol phase, (g) the butanol or pentanol phase is concentrated to a solids content of 50–70% to form a first concentrate, (h) the first concentrate of step (g) is diluted with sufficient water and ethanol to obtain an aqueous alcohol solution of 5 to 20 weight percent dry extract in 20 to 60 weight percent aqueous ethanol, (i) the aqueous alcohol solution is extracted with an aliphatic or cycloaliphatic solvent with a boiling point of approximately 60° to 100° C. to further remove the alkylphenol compounds, forming a water phase, (j) the water phase is concentrated under reduced pressure to form a second concentrate, (k) the second concentrate of step (j) is taken up in a mixture of water and acetone in a ratio of 10:90 to 60:40 weight percent, fed onto a column filled with a cross-linked polyvinyl pyrrolidone substrate and eluted with said mixture of water and acetone in a ratio of 10:90 to 60:40 weight percent to produce an eluate, and (l) the eluate is dried at a maximum temperature of 60° to 80° C. to recover a dry extract with a water content of less than 5%.

16. A method according to claim 15, wherein the method steps (d) and (e) are left out and the filtered solution remaining at the end of step (c) is processed further according to steps (f) to (l), and whereby in step (f) 10 to 30 weight percent of sodium chloride or ammonium sulfate is optionally added to the diluted solution.

17. A method according to claim 15, wherein said butanol in step (f) thereof is n-butanol.

18. A method according to claim 15, wherein instead of method steps (e) to (l) the following method steps (e') to (l') are carried out:

(e') the methylethylketone containing extract is concentrated to a solids content of 50–70% and is diluted with water and ethanol so that a diluted solution is obtained which contains 50 weight percent of water and 50 weight percent of ethanol with a solids content of 10 weight percent, (f') an aqueous solution of lead acetate, lead hydroxide acetate or lead nitrate, or an aqueous suspension of lead hydroxide, is added to the diluted solution until a change in color from brown to umber takes place, and a precipitate that is formed is removed to form an aqueous alcohol solution, (g') the aqueous alcohol solution is extracted with an aliphatic or cycloaliphatic solvent with a boiling point of approximately 60° to 100° C. to further remove the alklyphenol compounds, forming an extracted aqueous alcohol solution (h') the extracted aqueous alcohol solution is concentrated under reduced pressure to a maximum ethanol content of approximately 5% and ammonium sulfate is added to a content of 20 weight percent to form an ammonium sulfate solution, (i') the ammonium sulfate solution is extracted with a mixture of methylethylketone and ethanol in a ratio of 8:2 to 5:5, to form an organic phase, and (j') the organic phase is concentrated to a solids content of 50 to 70 weight percent to form a concentrate, (k') the concentrate is taken up in a mixture of water and acetone in a ratio of 10:90 to 60:40 weight percent, fed onto a column filled with a cross-linked polyvinyl pyrrolidone substrate and eluted with said mixture of water and acetone in a ratio of 10:90 to 60:40 weight percent to form an eluate, and (l') the eluate is dried at a maximum temperature of 60° to 80° C. to recover a dry extract with a water content of less than 5%.

19. In a method of preparing an extract of Ginkgo biloba leaves for intravenous administration, wherein said extract contains most of the flavone glycosides, ginkgolides and bilobalides present in the leaves from which said extract is derived, wherein said leaves contain also a predetermined amount of substances causing serum-precipitating or hemagglutinating properties, the improvement comprising including in said method a chromatographic treatment with cross-linked polyvinyl pyrrolidone or a polyamide substrate, thereby reducing the level of said serum-precipitating or hemagglutinating substances below said predetermined amount.

20. A method according to claim 19, wherein the chromatographic treatment is carried out with a mixture of water and a $C_{1-4}$-alcohol, or a mixture of water and a $C_{3-4}$-ketone, as an eluant.

* * * * *

UNITED STATES PATENT AND TRADEMARK OFFICE
CERTIFICATE OF CORRECTION

PATENT NO. : 5,512,286
DATED : April 30, 1996
INVENTOR(S) : Klaus-Peter SCHWABE

It is certified that error appears in the above-indentified patent and that said Letters Patent is hereby corrected as shown below:

| Column | Line | |
|---|---|---|
| 2 | 18-28 | Delete. |
| 3 | 34 | Change "$D_{1-4}$-alcohol" to --$C_{1-4}$-alcohol--. |
| 3 | 37 | Change "moisture" to --mixture--; change "$C_{1-14}$-alcohol." to --$C_{1-4}$-alcohol.--. |

Signed and Sealed this

Twenty-ninth Day of October 1996

Attest:

BRUCE LEHMAN

*Attesting Officer*     *Commissioner of Patents and Trademarks*